(12) United States Patent
Gagnon

(10) Patent No.: US 10,253,063 B2
(45) Date of Patent: *Apr. 9, 2019

(54) PROTEIN PURIFICATION IN THE PRESENCE OF NONIONIC ORGANIC POLYMERS AT ELEVATED CONDUCTIVITY

(71) Applicant: AGENCY FOR SCIENCE, TECHNOLOGY AND RESEARCH, Connexis (SG)

(72) Inventor: Peter Stanley Gagnon, Centros (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 106 days.

This patent is subject to a terminal disclaimer.

(21) Appl. No.: 14/769,099

(22) PCT Filed: Feb. 27, 2014

(86) PCT No.: PCT/SG2014/000089
§ 371 (c)(1),
(2) Date: Aug. 19, 2015

(87) PCT Pub. No.: WO2014/133460
PCT Pub. Date: Sep. 4, 2014

(65) Prior Publication Data
US 2016/0009758 A1    Jan. 14, 2016

Related U.S. Application Data

(60) Provisional application No. 61/770,890, filed on Feb. 28, 2013.

(51) Int. Cl.
*C07K 1/16* (2006.01)
*C07K 1/30* (2006.01)
*C07K 16/06* (2006.01)
*C07K 16/36* (2006.01)

(52) U.S. Cl.
CPC .................. *C07K 1/16* (2013.01); *C07K 1/30* (2013.01); *C07K 16/065* (2013.01); *C07K 16/36* (2013.01)

(58) Field of Classification Search
None
See application file for complete search history.

(56) References Cited

U.S. PATENT DOCUMENTS

| | | | |
|---|---|---|---|
| 4,814,098 A | 3/1989 | Inada et al. | |
| 9,637,724 B2 * | 5/2017 | Gagnon | C12N 7/00 |
| 9,695,216 B2 * | 7/2017 | Gagnon | B01D 15/34 |
| 2002/0099174 A1 * | 7/2002 | Johnston | B01D 37/02 |
| | | | 530/364 |
| 2007/0244305 A1 | 10/2007 | Parkkinen | |
| 2009/0292109 A1 * | 11/2009 | Gronke | C07K 1/30 |
| | | | 530/344 |
| 2010/0204455 A1 | 8/2010 | Gervais et al. | |
| 2012/0101262 A1 | 4/2012 | Arunakumari et al. | |
| 2015/0148526 A1 * | 5/2015 | Gagnon | C07K 1/20 |
| | | | 530/390.5 |
| 2015/0183852 A1 * | 7/2015 | Gagnon | C07K 16/00 |
| | | | 530/387.3 |
| 2015/0183879 A1 * | 7/2015 | Gagnon | C07K 16/00 |
| | | | 530/383 |
| 2015/0376230 A1 * | 12/2015 | Gagnon | 424/423 |
| 2015/0376231 A1 * | 12/2015 | Gagnon | B01D 15/36 |
| | | | 530/388.22 |
| 2016/0009759 A1 * | 1/2016 | Gagnon | C07K 1/30 |
| | | | 530/417 |
| 2016/0115194 A1 * | 4/2016 | Gagnon | C07K 1/34 |
| | | | 530/387.1 |
| 2016/0362446 A1 * | 12/2016 | Gagnon | C07K 16/00 |
| 2016/0362447 A1 * | 12/2016 | Gagnon | C07K 1/145 |
| 2016/0362448 A1 * | 12/2016 | Gagnon | B01D 15/265 |
| 2017/0057992 A1 * | 3/2017 | Gagnon | C07K 16/065 |

FOREIGN PATENT DOCUMENTS

| EP | 1581644 A1 | 6/2007 |
|---|---|---|
| JP | 63-066196 | 3/1988 |
| JP | S63-66196 | 3/1989 |
| JP | 2008-500959 | 1/2008 |
| JP | 2006-517415 | 10/2015 |
| WO | 2009/149067 | 12/2009 |
| WO | WO 2010/062244 A1 | 6/2010 |
| WO | 2012/169970 | 12/2012 |

(Continued)

OTHER PUBLICATIONS

Lu, Yi et al, "Ac electrokinetics of physiological fluids for biomedical applications." J. Lab. Automation. (2014) p. 1-10.*
Conductivity table on the MIT server, http://myweb.wit.edu/sandinic/Research/conductivity%20v%20concentration.pdf, available Oct. 3, 1999.*
The sales literature for CUNO filters, pamphlet LITZPSC1.EU-0102, available 2007.*
Vigna, Camila R. M. et al, "Poly(methyloctylsiloxane) immobilized on silica as a sorbent for solid-phase extraction of some pesticides." J. Chrom. A (2006) 1114 p. 211-215.*
The Labsource catalog page for GE Cameo filters, https://www.labsource.com/1224766msircameonylonsyringefilterwithprefilter.html, downloaded Jul. 24, 2017.*
The Corning filtration guide, https://www.corning.com/media/worldwide/cls/documents/CLS-FIL-004%20REV4%DL.pdf, downloaded Jul. 24, 2017.*

(Continued)

*Primary Examiner* — Fred H Reynolds
(74) *Attorney, Agent, or Firm* — Pillsbury Winthrop Shaw Pittman, LLP

(57) ABSTRACT

A method of purifying a desired protein from a preparation includes providing the preparation in a form having less than about 5% of the chromatin residing in the original production medium, contacting the preparation with a nonionic organic polymer in an amount sufficient to cause the desired protein to precipitate or adsorb on a nonionic hydrophilic surface, and adjusting a salt concentration before or during the contacting step, the adjusting step providing a sufficient salt concentration to produce a conductivity greater than physiological conductivity.

10 Claims, No Drawings

(56) References Cited

FOREIGN PATENT DOCUMENTS

| WO | 2012169970 A1 | 12/2012 |
|---|---|---|
| WO | 2013/180648 | 12/2013 |
| WO | 2013/180650 | 12/2013 |

OTHER PUBLICATIONS

Cole Palmer sales literature for filters, pamphlet 3014.IN, available 2011.*

The Fisher Scientific catalog page for Millipore glass filters, https://www.fishersci.com/shop/products/emdmilliporeglassfiberfilters46/p108537, downloaded Jul. 24, 2017.*

International Search Report dated Jun. 12, 2014 in International Patent Application No. PCT/SG2014/000089 (4 Pages).

Ingham, Kenneth, "Precipitation of proteins with polyethylene glycol: Characterization of albumin", Archives of Biochemistry and Biophysics, vol. 186, Issue 1, Feb. 1978, pp. 106-113.

Yamamoto, Keith R. et al., Virology, "Rapid Bacteriophage Sedimentation in the Presence of Polyethylene Glycol and its Application to Large-Scale Virus Purification", vol. 40, Issue 3, Mar. 1970, pp. 734-744.

Branston, Steve et al., "Precipitation of filamentous bacteriophages for their selective recovery in primary purification", Biotechnology and Bioprocess Engineering, vol. 28, Issue 1, Jan. 2012, pp. 129-136.

Lee, Jeremy et al., "Principles and Applications of Steric Exclusion Chromatography", vol. 1270, Dec. 28, 2012, pp. 162-170.

Gagnon, Peter et al., "High productivity purification of immunoglobulin G monoclonal antibodies on starch-coated magnetic nanoparticles by steric exclusion of polyethylene glycol", Journal of Chromatography A, vol. 1324, Jan. 10, 2014, pp. 171-180.

Gan, Hui Theng et al., "Characterization and removal of aggregates formed by nonspecific interaction of IgM monoclonal antibodies with chromatin catabolites during cell culture production", Journal of Chromatography A, vol. 1291, May 24, 2013, pp. 33-40.

European Office Action dated Jul. 14, 2017 for European Patent Application No. 14757178.0.

Office Action dated Nov. 27, 2017, for related U.S. Appl. No. 14/769,101.

Advisory Action dated Jan. 30, 2018, for related U.S. Appl. No. 14/769,101.

Official Action dated Nov. 20, 2017 for related European Patent Application No. 14757178.0.

English translation of Japanese Patent Office Action dated Nov. 21, 2017, for related Japanese Patent Application No. 2015-560142.

Japanese Patent Application No. 2015-560142, Office Action dated Jul. 3, 2018.

* cited by examiner

PROTEIN PURIFICATION IN THE PRESENCE OF NONIONIC ORGANIC POLYMERS AT ELEVATED CONDUCTIVITY

STATEMENT OF RELATED APPLICATIONS

This application claims priority to U.S. Provisional Application No. 61/770,890, filed Feb. 28, 2013, which is incorporated herein by reference in its entirety.

BACKGROUND

Embodiments disclosed herein relate to methods for purification of proteins, including antibodies, including IgG antibodies.

The technique of protein precipitation with non-ionic organic polymers, such as polyethylene glycol (PEG), is known. It is most often used at low salt concentrations, in the absence of added salt, but exceptions are known (D. Gervais et al, US Patent Application 2010/0204455 A1; K. Ingham, Arch. Biochem. Biophys. 186 (1978) 106-113; K. Yamamoto et al, Virology, 40 (1970) 734-744; S. Branston et al, Biotechnol. Progr. 28 (2012) 129-136).

The technique of Steric Exclusion Chromatography is known (J. Lee et al, J. Chromatogr. A 1270 (2012) 162-170; see also PCT/SG2012/000199, incorporated herein by reference and attached as Appendix A). It exploits nonionic hydrophilic surfaces on which retention of a desired product is induced by a nonionic organic polymer such as PEG. Elevated NaCl concentrations have been reported to increase virus binding efficiency (Lee et al supra). Conducting the technique on fluidized particles in the presence of elevated concentrations of NaCl has been reported to increase recovery and purity of IgG preparations (P. Gagnon et al, J. Chromatogr. A, 1324:171-180, (2014).

Methods for reducing the content of chromatin from cell culture harvests containing monoclonal antibodies have been described (H. Gan et al, J. Chromatogr. A, 1291 (2013) 33-40. Chromatin is known to include DNA and histone proteins in stable associations known as nucleosomes. Gan et al reported that chromatin and its catabolites also form associations with antibodies that limit the efficacy of subsequent fractionation methods. They reported methods that achieved chromatin reduction of 99%, and further reported that such reduction improved the quality of purification obtained by cation exchange chromatography. A variation of a technique reported by Gan et al has been reported by Gagnon et al (2013, supra) to improve recovery and purity of IgG fractionated by steric exclusion chromatography on fluidized hydrophilic particles.

SUMMARY

A method of purifying a desired protein from a preparation comprising providing the preparation in a form having less than about 5% of the chromatin residing in the original production medium, contacting the preparation with a non-ionic organic polymer in an amount sufficient to cause the desired protein to precipitate or, adsorb on a nonionic hydrophilic surface, and adjusting a salt concentration before or during the contacting step, the adjusting step providing a sufficient salt concentration to produce a conductivity greater than physiological conductivity.

DETAILED DESCRIPTION

It has been surprisingly discovered that PEG-mediated fractionation methods performed on an impure preparation of a desired protein that has been conditioned to remove at least 95% of the chromatin, where the PEG-mediated method includes at least one stage where the desired protein is contacted with additional salt sufficient to produce a greater than physiological conductivity, can achieve a higher degree of desired-protein purification than current practice with the known high-functioning method of bioaffinity chromatography.

In certain embodiments, the methods disclosed herein provide multi-step methods for purification of a desired antibody from an impure preparation that has been conditioned to remove at least 95% of the chromatin, including the steps of (i) contacting the impure preparation with a non-ionic organic polymer in an amount sufficient to cause the desired antibody to be precipitated, in the simultaneous presence of a concentration of salt sufficient to produce a conductivity greater than normal physiological conductivity, (ii) optionally reducing or eliminating salt from the mixture, (iii) reducing the nonionic organic polymer to a concentration insufficient to maintain the desired antibody in a precipitated state, leaving highly purified antibody which may be further purified by additional fractionation methods, if desired.

In certain embodiments, the methods disclosed herein provides multi-step methods for purification of a desired antibody from an impure preparation that has been conditioned to remove at least 95% of the chromatin, including the steps of (i) contacting the impure preparation with a non-ionic organic polymer in an amount sufficient to cause the desired antibody to be precipitated, (ii) adding salt to a concentration of salt sufficient to produce a conductivity greater than normal physiological conductivity, (iii) reducing or eliminating salt from the mixture, (iii) reducing the nonionic organic polymer to a concentration insufficient to maintain the desired antibody in a precipitated state, in the presence of at least one electropositive surface, and (iv) separating the at least one electropositive surface from the preparation, leaving highly purified antibody which may be further purified by additional fractionation methods, if desired.

In certain embodiments, the methods disclosed herein provides multi-step methods for purification of a desired antibody from an impure preparation that has been conditioned to remove at least 95% of the chromatin, including the steps of (i) contacting the impure preparation with a non-ionic organic polymer in an amount sufficient to cause the desired antibody to be precipitated, in the simultaneous presence of a concentration of salt sufficient to produce a conductivity greater than normal physiological conductivity, (ii) reducing the nonionic organic polymer to a concentration insufficient to maintain the desired antibody in a precipitated state, leaving highly purified antibody which may be further purified by additional fractionation methods, if desired.

In certain embodiments, the methods disclosed herein provides multi-step methods for purification of a desired antibody from an impure preparation that has been conditioned to remove at least 95% of the chromatin, including the steps of (i) contacting the impure preparation with a non-ionic organic polymer in an amount sufficient to cause the desired antibody to be accreted on the surface of a monolith with a non-ionic hydrophilic surface, in the presence of salt sufficient to produce a conductivity greater than normal physiological conductivity, (ii) washing the accreted antibody with a clean solution of polymer and salt, then optionally washing the accreted antibody with a clean solution of polymer lacking or deficient in salt, (iii) then eluting the purified antibody by reducing the nonionic organic polymer to a concentration insufficient to maintain the desired, antibody in an accreted state.

In certain embodiments, the methods disclosed herein provides multi-step methods for purification of a desired antibody from an impure preparation that has been conditioned to remove at least 95% of the chromatin, including the steps of (i) contacting the impure preparation with a non-ionic organic polymer in an amount sufficient to cause the desired antibody to be precipitated, (ii) adding salt to a concentration of salt sufficient to produce a conductivity greater than normal physiological conductivity, (iii) reducing or eliminating salt from the mixture, (iii) reducing the nonionic organic polymer to a concentration insufficient to maintain the desired antibody in a precipitated state, in the presence of at least one electropositive surface, and (iv) separating the at least one electropositive surface from the preparation, leaving highly purified antibody which may be further purified by additional fractionation methods, if desired.

In any of the previous embodiments, nonionic hydrophilic particles may optionally be present at any stage of the method. In some such embodiments, the nonionic hydrophilic particles may have an average size of 10 nanometers, or 100 nanometers, or 1 micron, or 10 microns, or 100 microns, or an intermediate or larger size. In some embodiments, the particle may be magnetic or paramagnetic, enabling their collection in a magnetic field or on a magnetic surface.

In certain embodiments, the method may be practiced with dead-end filtration media, where the precipitate is retained while unprecipitated contaminants pass through, and are thereby eliminated.

In certain embodiments, the method may be practiced with centrifugation, where the precipitate is sedimented, enabling the disposal of the contaminant-containing supernatant.

In some embodiments where the method is practiced in a centrifugal format, an impure IgG preparation from which at least 95% or the chromatin has been removed is precipitated by the addition of polyethylene glycol with an average molecular weight of 6000 (PEG-6000) and NaCl to produce a precipitating solution contain 19% PEG-6000 and 0.8 M NaCl. The precipitate is sedimented by centrifugation and the contaminant-containing supernatant is discarded. The precipitated IgG is optionally resuspended in a fresh solution of 19% PEG-6000, 0.8 M NaCl and a buffering substance to confer a desired pH value, resedimented, and the supernatant discarded. The precipitate may then be optionally resuspended in a fresh solution of PEG-6000, and a buffering substance to confer a desired pH value, but lacking or deficient in salt; then resedimented, after which the supernatant is discarded. The precipitated highly purified IgG is then resolubilized in a buffer formulated to be consistent with any follow-on fractionation step or application of the purified antibody that may be desired.

In some embodiments where the method is practiced in a filtration format, an impure IgG preparation from which at least 95% or the chromatin has been removed is precipitated by the addition of polyethylene glycol with an average molecular weight of 6000 (PEG-6000) and NaCl to produce a precipitating solution contain 19% PEG-6000 and 0.8 M NaCl. The precipitate is captured on a membrane filter with an average pore size of 0.22 microns, while the contaminant-containing supernatant flows through the membrane and is discarded. The precipitated IgG is optionally resuspended in a fresh solution of 19% PEG-6000, 0.8 M NaCl and a buffering substance to confer a desired pH value, refiltered, and the supernatant discarded. The precipitate may then be optionally resuspended in a fresh solution of PEG-6000, and a buffering substance to confer a desired pH value, but lacking or deficient in salt; then refiltered, after which the supernatant is discarded. The precipitated highly purified IgG is then resolubilized in a buffer formulated to be consistent with any, follow-on fractionation step or application of the purified antibody that may be desired, and optionally filtered through the same membrane previously used to separate the precipitated antibody from soluble contaminants in the supernatant.

In some embodiments where the method is practiced in a filtration format and employs nonionic hydrophilic particles as nucleation centers, an impure IgG preparation from which at least 95% of the chromatin has been removed, starch particles amounting to 5% w/v are added before the IgG is forced onto the particles by the addition of polyethylene glycol with an average molecular weight of 6000 (PEG-6000) and NaCl to produce a precipitating solution contain 19% PEG-6000 and 0.8 M NaCl. IgG accretes on the particles instead of forming purely-IgG precipitates. The particles with accreted IgG are captured on a membrane filter with an average pore size of 0.22 microns, while the contaminant-containing supernatant flows through the membrane and is discarded. The particles with accreted IgG are optionally resuspended in a fresh solution of 19% PEG-6000, 0.8 M NaCl and a buffering substance to confer a desired pH value, refiltered, and the supernatant discarded. The particles with accreted IgG may then be optionally resuspended in a fresh solution of PEG-6000, and a buffering substance to confer a desired pH value, but lacking or deficient in salt; then refiltered, after which the supernatant is discarded. The highly purified IgG is then resolubilized in a buffer formulated to be consistent with any follow-on fractionation step or application of the purified antibody that may be desired, and filtered through the membrane, which retains the starch particles while the purified IgG is retained by the membrane and discarded.

In some embodiments where the method is practiced in a magnetic particle format and employs nonionic hydrophilic particles as nucleation centers, an impure IgG preparation from which at least 95% of the chromatin has been removed, starch-coated magnetic nanoparticles amounting to 1% w/v are added before the IgG is forced onto the particles by the addition of polyethylene glycol with an average molecular weight of 6000 (PEG-6000) and NaCl to produce a precipitating solution contain 19%. PEG-6000 and 0.8 M NaCl. IgG accretes on the particles instead of forming purely-IgG precipitates. The particles with accreted IgG are captured in a magnetic field, while the contaminant-containing supernatant is discarded. The particles with accreted IgG are optionally resuspended in a fresh solution of 19% PEG-6000, 0.8 M NaCl and a buffering substance to confer a desired pH value, recaptured in a magnetic field, and the supernatant discarded. The particles with accreted IgG may then be optionally resuspended in a fresh solution of PEG-6000, and a buffering substance to confer a desired pH value, but lacking or deficient in salt; then recaptured in a magnetic field, after which the supernatant is discarded. The highly purified IgG is then resolubilized in a buffer formulated to be consistent with any follow-on fractionation step or application of the purified antibody that may be desired. The nanoparticles are removed by capturing them in a magnetic field.

In some embodiments where the method is practiced in a magnetic particle format and employs nonionic hydrophilic particles as nucleation centers, an impure IgG preparation from which at least 95% of the chromatin has been removed, starch-coated magnetic nanoparticles amounting to 1% w/v are added before the IgG is forced onto the particles by the addition of polyethylene glycol with an average molecular weight of 6000 (PEG-6000) and NaCl to produce a precipitating solution contain 19% PEG-6000 and 0.8 M NaCl. IgG accretes on the particles instead of forming purely-IgG precipitates. The particles with accreted IgG are captured in a magnetic field, while the contaminant-containing supernatant is discarded. The particles with accreted IgG are optionally resuspended in a fresh solution of 19% PEG-6000, 1.0 M NaCl, 50 mM Tris, pH 8.0, recaptured in a magnetic field, and the supernatant discarded. The highly purified IgG is then resolubilized. The nanoparticles are removed by capturing them in a magnetic field, and the IgG is applied to a column packed with a hydrophobic anion exchanger such as Capto adhere (GE Healthcare), where the antibody binds. The antibody is then eluted by reducing the NaCl concentration to 300 mM.

In some embodiments where the method is practiced in a fixed-bed chromatography format and employs a monolith with a nonionic hydrophilic surface as nucleation center for accretion of IgG, an impure IgG preparation from which at least 95% of the chromatin has been removed is forced onto the monolith surface in the presence of polyethylene glycol with an average molecular weight of 6000 (PEG-6000) and NaCl to produce a precipitating solution contain 19% PEG-6000 and 0.8 M NaCl. IgG accretes on the monolith surface instead of producing precipitates. The contaminant-containing supernatant flows through the monolith and is discarded. The monolith is washed with a fresh solution of 19% PEG-6000, 1.0 M NaCl, 50 mM Tris, pH 8.0. The highly purified IgG is eluted from the monolith by applying a solution of 1.0 M NaCl, 50 mM Tris, pH 8.0. In some such embodiments where it is desired to conduct additional purification, the IgG is optionally applied to a column packed with a hydrophobic anion exchanger such as Capto adhere (GE Healthcare), where the antibody binds. The antibody is then eluted by reducing the NaCl concentration to 300 mM. In a closely related embodiment, the final wash buffer contains 19% PEG-6000, 50 mM MES, pH 6.0 and the IgG is eluted in 50 mM MES pH 6.0 and applied to a cation exchanger and subsequently eluted by increasing the salt concentration and/or by increasing the pH. In a closely related embodiment, the final wash buffer contains 19% PEG-6000, 50 mM sodium phosphate, 100 mM NaCl, pH 7.0 and the IgG is eluted in 50 mM sodium phosphate, 100 mM NaCl, pH 7.0 and applied to a hydrophobic cation exchanger for additional purification. In a closely related embodiment, the final wash buffer contains 19% PEG-6000, 10 mM sodium phosphate, pH 7.0 and the IgG is eluted in 10 mM sodium phosphate, pH 7.0 and applied to hydroxyapatite for additional purification. It will be recognized that all of the additional purification steps described above have the effect of removing residual PEG from an IgG preparation, in addition to removing additional contaminants that may be present.

In some embodiments, the desired protein may be an antibody. In some embodiments, the desired protein may be an IgG antibody. In some embodiments, the desired protein may be an IgM antibody. In some embodiments, the desired protein may be a monoclonal antibody. In some embodiments, the desired protein may be a non-antibody protein. In some embodiments, the desired protein may be a clotting factor. In some embodiments, the desired protein may be fibrinogen. In some embodiments, the desired protein, may be Factor VIII. In some embodiments, the desired protein may be a complex or Factor VIII and von Willebrand factor, where the complex is also known as anti-hemophiliac factor.

In certain embodiments, a concentration of salt sufficient to produce a conductivity greater than normal physiological conductivity may be substantially greater than normal physiological conductivity. Where normal conductivity may range from 12 to 16 mS/cm, a value considered to be substantially greater may include 20 mS/cm, or 30 mS/cm, or 40 mS/cm, or 50 mS/cm, or 60 mS/cm, or 70 mS/cm, or 80 mS/cm, or 90 mS/cm, or 100 mS/cm, or 150 mS/cm, or 200 mS/cm, or an intermediate or higher value, for example up to the conductivity of a saturated solution of NaCl. Experimental data indicate the most effective contaminant reduction and IgG recovery may be obtained in a range from about 50 to 150 mS/cm, corresponding to a concentration of NaCl ranging from about 0.5 to about 1.5 M. In other cases, the term greater than physiological conductivity may be understood to be 17, or 18, or 19 mS/cm, or an intermediate value. It is to be understood that every IgG behaves differently and the components of the impure preparation in which the IgG resides also impose an influence, so it will be necessary to conduct simple experiments to determine the most favorable conductivity to accommodate a particular IgG preparation. It is important to realize that in addition to the advantage of enabling PEG precipitation to achieve a higher level of purity, the reduction of contaminants, including acidic contaminants, also reduces the necessary capacity of the at least one electropositive surface, which renders it more effective and may also permit the dimensions of that surface to be reduced.

In certain embodiments, the salt employed to increase conductivity may be a neutral salt, such as sodium chloride, potassium chloride, sodium acetate, potassium acetate. In certain embodiments the salt may be a chaotropic salt, such as guanidine acetate, guanidine hydrochloride, guanidine sulfate, phosphate, sodium thiocyanate, or potassium thioscyanate, among others. In certain embodiments, the use of precipitating salts will be avoided, including sodium sulfate, potassium sulfate, ammonium sulfate, sodium citrate, potassium citrate, ammonium citrate, potassium phosphate, because they have a strong tendency to create a spontaneous phase separation, producing a concentrated PEG solution floating on top of a concentrated salt solution. For most purposes, and especially as a starting point, NaCl will generally be the salt of choice.

In certain embodiments, the concentration of salt is greater than 2.0 M, or greater than 2.5 M, or greater than 3 M, or greater than 4 M, up to a saturated solution. In some such embodiments, the salt is NaCl. In some such embodiments, the salt is KCl.

In certain embodiments, during the process stage where the conductivity is above physiological conductivity, especially including values substantially above physiological conductivity, the need to optimize operating pH may be reduced or suspended. At low conductivity values, pH modulates charge interactions among proteins. When proteins are at their isoelectric point, their net charge is zero and they are minimally self-repellant. When pH is above their isoelectric point, they have a net negative charge, and with increasing pH become increasingly self-repellant. When pH is below their isoelectric point, they have a net positive charge, and with decreasing pH become increasingly self-repellant. Thus when a given IgG is at or close to its isoelectric point, it generally favors precipitation by PEG. Since salt ions compete with electrostatic interactions between charged bodies in solution, they reduce the degree of repellency between proteins at pH values away from their isoelectric point, which reduces or abolishes the effect of pH. The practical significance in the context of the disclosed methods is that in some embodiments, the presence of salts at concentrations that produce high conductivities largely eliminates the need to adjust pH. For the purposes of customizing the method to a particular IgG in a particular impure preparation, a neutral pH of 7.0 makes a good starting point, and it may be unnecessary to adjust it.

In some embodiments where a salt is present at a concentration greater than 2 M, the pH of the solution is 7, or 8, or 8.5, higher, or 6, or 6.5, or another value between 6 and 8.5, or lower than 6.

In some such embodiments, the salt is NaCl or KCl, or a combination thereof, or a combination of either or both with other salts.

In some embodiments, the nonionic organic polymer may be polyethylene glycol (PEG), or polypropylene glycol, or dextran, or cellulose, or starch, or polyvinylpyrrolidone, among others, or a combination.

In some embodiments, the nonionic organic polymer will be PEG with a polymer size of about 2,000 Daltons (D), or 3,000 D, or 4,000 D, or 5,000 D, or 6,000 D, or 8,000 D, or 10,000 D, or 12,000, D, or an intermediate polymer size. Experience documents that the smaller the average polymer size, the higher the concentration required to achieve precipitation. This is not simply to adjust for mass; there is a progressive effect mediated by the fact that the effectivity of PEG polymers is proportional to their hydrodynamic radius independent mass, so that PEG polymers of the same mass but different degrees of branching have different abilities to mediate precipitation. In some embodiments, a combination of polymer sizes may be employed.

In some embodiments, the PEG will be PEG-6000, and the concentration of PEG required to achieve IgG precipitation at physiological or lower conductivity values, or to maintain the IgG in a precipitated state at those conductivity values, may range from 12% to 18%, or 14-16%. In some embodiments, the concentration of PEG-6000 in a concentration of salt sufficient to produce a conductivity of about 80 mS/cm, such as 1 M NaCl, will need to be elevated in order to achieve IgG precipitation and/or maintain IgG in a precipitated state. In one such embodiment where the concentration of PEG-6000 required to achieve precipitation at physiological concentration is 15-16%, the concentration of PEG-6000 required to achieve precipitation in the presence of 1 M NaCl is 18-22%. This reflects a known but generally overlooked effect of salt whereby it decreases the hydrodynamic radius of the PEG. These concentrations can be used as guidelines or starting points, with the understanding that accommodating the unique individual characteristics of each IgG clone and the impure preparation in which it resides will require optimization.

In some embodiments, the impure IgG preparation may consist of a cell culture harvest, such as from mammalian cells, yeasts, or bacteria. In some embodiments, the impure preparation may consist of an extract of cultured cells. In some embodiments, the impure IgG preparation may consist of a bodily fluid, such as plasma, serum, milk or other bodily fluids.

In some embodiments, the impure preparation may be a cell culture harvest that has been processed to remove cells. In one such embodiment, the harvest may be previously conditioned by physical methods such as centrifugation and filtration.

In all of the previous embodiments, practicing the disclosed methods on an impure preparation that has been conditioned to remove at least 95% clearance of chromatin and associated catabolites disproportionately increases the ability of the system to achieve high purification. In some such embodiments, the harvest may be conditioned by contact with one or more positively charged surfaces where the positive charge is conferred by multivalent organic ions immobilized on the surface. In another such embodiment, the conditioning method involves contacting the desired product preparation with soluble multivalent organic ions. In another such embodiment, the conditioning method involves contacting the desired product preparation with soluble and/or insoluble multivalent organic ions.

In some embodiments, the preparation can be reduced in chromatin to a level at least 95% lower than in the original biological source by a conditioning method that involved contacting the harvest with one or more multivalent organic ions. In some such embodiments, the multivalent organic ion is electropositive.

In some embodiments, a soluble electropositive multivalent ion comprises one selected from the group of cations consisting of methylene blue, ethacridine, chlorhexidine, benzalkonium chloride, cetyl trimethyl ammonium bromide, and combinations thereof.

In some embodiments, the multivalent ion is insoluble by virtue of being covalently attached to a surface.

In some embodiments, the insoluble electropositive multivalent ion is selected from the group consisting of a primary amino group, a secondary amino group, a tertiary amino group, a quaternary amino group, a complex cation containing more than one positive charges conferred by one or more types of amino groups, and combinations thereof.

In some embodiments, the insoluble electropositive multivalent ion is tris(2-aminoethyl)amine (TREN).

In some embodiments, the multivalent organic ion is electronegative.

In some embodiments, the soluble electronegative multivalent ion is selected from the group consisting of heptanoic acid, heptenoic acid, octanoic acid, octenoic acid, nonanoic acid, nonenoic acid, decanoic acid, methyl blue, and combinations thereof.

In some embodiments, the insoluble electronegative multivalent ion is selected from the group consisting of a phospho group, a carboxyl group, a sulfo group, a complex anion containing more than one negative charge conferred by one or more types of negatively charged groups, and combinations thereof.

In some embodiments, the insoluble complex electronegative multivalent may be iminodiacetic acid or nitriloacetic acid.

In some embodiments, the insoluble multivalent ion has a 1:1 affinity for a metal ion.

In some embodiments, allantoin may be optionally present at a supersaturating concentration in a range selected from the group consisting of (a) from about 0.6% to about 50%, (b) from about 0.7% to about 20%, (c) from about 0.8% to about 10%, (d) from about 0.9% to about 5%, (e) from about 1% to about 2%, and an intermediate ranges thereof.

In one or more of the preceding embodiments, conditioning the impure preparation with organic multivalent ions comprises contacting the sample with a soluble electropositive organic additive. In some such embodiments, the electropositive organic additive comprises at least one species from the group consisting of ethacridine, methylene blue, cetyltrimethylammonium bromide. In some such embodiments, the concentration of such a species, or aggregate concentration of a combination of species is in the range of 0.001 to 1%, or 0.01 to 0.1%, or 0.02 to 0.05%, or 0.01 to 0.1%, or an intermediate value. In some such embodiments the pH of the preparation may be adjusted up to an alkaline value that does not cause significant reduction of recovery of the desired IgG. In one such embodiment, the pH may be adjusted up to a pH value within a half pH unit of the antibody isoelectric point, or more if experimental results indicate that antibody recovery is acceptable, but such adjustments are generally not necessary. To the extent that any pH adjustment is made, a value within 1 pH unit of the protein isoelectric point will suffice, or within 1.5 pH units, or within 2 pH units or more.

In one or more of the preceding embodiments, conditioning the impure preparation with organic multivalent ions comprises contacting the sample with a soluble electronegative organic additive. In some such embodiments, the electronegative organic additive comprises at least one species from the group consisting of heptanoic acid, heptenoic acid, octanoic acid, octeneoic acid, nonanoic acid, nonenoic acid, decanoic acid, methyl blue. In some such embodiments, the concentration of such a species, or total concentration of a combination of species is in the range of 0.001 to 10%, or 0.01 to 1%, or 0.1 to 0.5%. In some such embodiments the pH of the preparation may be adjusted down to an acidic value that does not cause significant reduction of recovery of the desired protein. In some such embodiments, the pH of the preparation may be adjusted to the range of 3.5 to 6.5, 4.0 to 6.0, 4.5 to 5.5, 5.0 to 5.3, 5.15 to 5.25, or 5.2, or another intermediate value.

In one or more of the preceding embodiments, conditioning the impure preparation with organic multivalent ions comprises contacting the sample with undissolved allantoin. In some such embodiments, the added allantoin resident in an impure preparation may amount to about 0.6% to 50%, or 0.7 to 20%, or 0.8 to 10%, or 0.9 to 5%, or 1 to 2%, or an intermediate value. In one or more of the preceding embodiments, the average particle size of the dry allantoin is selected to be the smallest size available, with the goal of achieving the highest total surface area of the undissolved allantoin in a supersaturated solution. In one such embodiment, the allantoin is granulated to produce a smaller particle size.

In some embodiments, where a multimodal organic ion immobilized on a solid surface is electropositive, the immobilized multimodal organic ion may be a nitrogen containing group, such as a primary amino group, or a secondary amino group, or a tertiary amino group, or a quaternary amino group, or a combination or polymer of such groups. In some such embodiments, the nitrogen-containing compound may be 2(aminoethyl)amine (TREN). In some embodiments, the positively charged nitrogen-containing group may be an imine, or a pyridine, or other electropositive group. In some embodiments, the positive charge of a nitrogen-containing compound may reside on a residue other than a nitrogen atom, such as a sulfur atom.

In one or more of the preceding embodiments, conditioning the impure preparation with organic multivalent ions comprises contacting the sample with a nonionic or zwitterionic surfactant at a concentration lower than its critical micelle concentration.

In one or more of the preceding embodiments, conditioning of the impure preparation with organic multivalent ions comprises (i) providing a first component which is a first solid substrate having an electronegative surface; (ii) contacting the impure preparation with the first component, wherein the operating conditions substantially prevent the binding of the desired protein to the first component; and (iii) separating the desired protein with a reduced chromatin content from the first component. In some such embodiments, the first electronegative surface may be accompanied by a second electronegative surface.

In one or more of the preceding embodiments, conditioning of the impure preparation with organic multivalent ions comprises (i) providing a first component which is a first solid substrate having an electropositive surface; (ii) contacting the impure preparation with the first component, wherein the operating conditions substantially prevent the binding of the desired protein to the first component; and (iii) separating the desired protein with a reduced chromatin content from the first component. In some such embodiments, the first electropositive surface bears residues of 2(aminoethyl)amine. In some such embodiments, the first electropositive surface may be accompanied by a second electropositive surface.

In one or more of the preceding embodiments, conditioning of the impure preparation with organic multivalent ions comprises (i) providing a first component which is a first solid substrate having an electropositive surface; (ii) providing a second component which is a second solid substrate having an electronegative surface; (iii) contacting the impure preparation with the first and second components, wherein the first and second components are configured such that the impure preparation may contact both components simultaneously, wherein the operating conditions substantially prevent the binding of the desired protein to the first or second components; and (iv) separating the desired protein with a reduced chromatin content from the first and second components. In some such embodiments, the first electropositive surface bears residues of 2(aminoethyl)amine (TREN).

In one or more of the preceding embodiments, conditioning of the impure preparation with organic multivalent ions comprises (i) contacting the impure preparation with at least one solid surface comprising at least one surface-bound ligand capable of binding a metal, wherein the surface-bound ligand capable of binding a metal is initially substantially devoid of a metal, wherein operating conditions are selected to substantially prevent the binding of the desired protein to the at least one solid surface and (ii) separating the impure preparation from the at least one surface-bound ligand.

In one or more of the preceding embodiments, an impure preparation already treated with a soluble electropositive or electronegative organic additive and/or a solid surface bearing an electronegative, electropositive, or metal affinity ligand, may be subsequently flowed through a device, the fluid-contact surface of which comprises positive charges.

In one embodiment illustrating application of a chromatin-directed clarification method, allantoin is added to a cell culture harvest in an amount of 1% (v/v). The cell culture may contain cells, or the cells may previously have been removed. Methylene blue is added to a concentration of 0.025% (w/v). Alternatively, ethacridine may be added to a concentration of 0.025%. Alternatively, 0.025% cetyl trimethyl ammonium bromide may be added to a concentration of 0.025%. Alternatively, a combination of these or other electropositive organic additives may be used at a combined concentration of 0.025%. The mixture is then incubated stirring for 2 hours. Particles bearing the electropositive metal affinity ligand 2(aminoethyl)amine (TREN) are added in an amount of 2-5% v:v. The mixture is incubated stirring for 4 hours then the solids are removed by any expedient means. The remaining solution containing the desired protein may be optionally flowed through a depth filter bearing positive charges on its fluid contact surface.

In another embodiment illustrating application of a chromatin-directed clarification method, allantoin is added to a cell culture harvest in an amount of 1% (v/v). The cell culture may contain cells, or the cells may previously have been removed. 0.7% heptanoic acid is added. Alternatively 0.4% octanoic acid is added. Alternatively 0.4% octenoic acid is added. Alternatively 0.3% pelargonic (nonanoic) acid is added. Alternatively 0.3% nonenoic acid is added. Alternatively 0.2% capric acid is added. Alternatively, 0.5% methyl blue is added. Alternatively, a combination of these or other electronegative organic additives may be used. The mixture is then incubated stirring for 2 hours. Particles bearing the electropositive metal affinity ligand 2(aminoethyl)amine (TREN) are added in an amount of 2-5% v:v. The mixture is incubated mixing for 4 hours then the solids removed by any expedient method. The remaining solution containing the desired protein may be optionally flowed through a depth filter bearing positive charges on its fluid contact surface.

In some embodiments, the degree of chromatin reduction of a particular conditioning method is estimated by measuring the degree of DNA reduction, and the degree of histone reduction, and averaging the two values. In some such embodiments, DNA is measured by an intercalating dye assay, while histones are typically measured by immunoassay. In some such embodiments, because the amount of histone is a direct function of the amount of chromatin, the total histone content can be measured by determining the content of 1 species of histone, and adjusting the quantity in proportion to the relative proportions of other histones in chromatin. For example, total histone might be estimated by measuring histone H1, then multiplying times 9 to account for the mass ratio of H1 to other histones in intact chromatin. Alternatively, total histone might be estimated by measuring H2a, H2b, H3, or H4, and multiplying the result from any one of them by 4.5. Alternatively, individual assays might be run for H1 and H2a, and H2b, and H3, and H4, and the results added together. DNA assays may alternatively be aided by polymerase chain reaction technology. However, experimental data indicate that using DNA to estimate total chromatin may cause total chromatin to be underestimated due to enzyme-mediated hydrolysis of the DNA following cell death during production. Histone and DNA assays may both require special extraction procedures to obtain accurate results.

In certain embodiments, the IgG preparation may be contacted with one or more antiviral compounds during one or more stages of the method. In some such embodiments, the one or more antiviral compounds are selected from the group consisting of ethacridine, methylene blue, benzalkonium chloride, chlorhexidine, cetyltrimethyl ammonium bromide, tri(n-butyl)phosphate.

In certain embodiments, nonionic hydrophilic particles employed during performance of the method are nanoparticles or microparticles. In certain such embodiments, the nonionic hydrophilic particles are porous. In certain embodiments, the particle size is between about 50 nm and about 500 µm, or is between about 50 nm and about 50 µm, or is between about 50 nm and about 4 µm, or is between about 50 nm and about 3 µm, or is between about 50 nm and about 1 µm, or is between about 100 nm and about 1, or is between about 200 nm and about 2 µm, or is between about 200 nm and about 500 nm, or is between about 500 nm and about 1 µm, or is between about 5 µm and about 50 µm.

In some embodiments, there are provided methods of purifying a desired protein from a preparation comprising providing the preparation in a form having less than about 5% of the chromatin residing in the original production medium, contacting the preparation with a nonionic organic polymer in an amount sufficient to cause the desired protein to precipitate or adsorb on a nonionic hydrophilic surface, and adjusting a salt concentration before or during the contacting step, the adjusting step providing a sufficient salt concentration to produce a conductivity greater than physiological conductivity.

In some embodiments, methods disclosed herein further comprise retaining the precipitated desired protein on a porous membrane, thereby allowing soluble contaminants to pass through the membrane.

In some embodiments, methods disclosed herein further comprise separating the precipitated desired protein from soluble contaminants by sedimenting the precipitate by means of centrifugation.

In some embodiments, the nonionic hydrophilic surface comprises one selected from the group consisting of a membrane, a monolith, particles, the particles being optionally magnetic, and combinations thereof.

In some embodiments, the method is carried out in a single integrated apparatus.

In some embodiments, the nonionic organic polymer is polyethylene glycol (PEG).

In some embodiments, an average polymer size of the nonionic organic polymer is in a range selected from the group consisting of (a) from about 1,500 Daltons to about 15,000 Daltons, (b) from about 2,000 Daltons to about 12,000 Daltons (c) from about 3,000 Daltons to about 10,000 Daltons, (d) from about 4,000 Daltons to about 8,000 Daltons, and (f) from about 5,000 Daltons to about 6,000 Daltons.

In some embodiments, the conductivity is at least 1 mS/cm greater than physiological conductivity. In some embodiments, the conductivity is greater than physiological conductivity by greater than about 1 mS/cm, 5 mS/cm, 10 mS/cm, 20 mS/cm, 40 mS/cm, 80 mS/cm, 160 mS/cm, up to a conductivity corresponding to a saturated solution of a selected solution of salt or salts, or an intermediate increment. In some embodiments, a range of conductivities greater than physiological may be from about 35 mS/cm to about greater than physiological conductivity by about 135 mS/cm is employed.

In some embodiments, the salt is selected from the group consisting of sodium chloride, potassium chloride, sodium acetate, potassium acetate, sodium thiocyanate, potassium thiocyanate, guanidinium hydrochloride, and combinations thereof.

In some embodiments, the salt is sodium chloride at a concentration selected from the group consisting of (a) from about 0.5 M to about 1.5 M, (b) from about 2.0 M to about 3.0 M, and intermediate ranges thereof.

In some embodiments, methods further comprise adjusting a pH to a range selected from the group consisting of (a) from about 5 to about 9, (b) from about 6 to about 8, (c) from about 6.5 to about 7.5, (d) from about 7.5 to about 8.5, and intermediate ranges thereof.

In some embodiments, the preparation is obtained from a biological source selected from the group consisting of a cell culture medium, an extract from cultured organisms, and a bodily fluid.

Terms below are defined so that the methods disclosed herein may be understood more readily. Additional definitions are set forth throughout the detailed description.

"Chromatin" refers the basic composition of chromosomes. In its intact form in living cells it dominantly comprises DNA and histone proteins, associated with smaller amounts of other proteins and peptides. It is organized into nucleosomes, which comprise an octamer of histone proteins including 2 each of histones 2a, 2b, 3, and 4, wrapped with 1.65 turns of DNA. Nucleosomes are linked in linear areas by sections of linker DNA, which are associated with histone H1. Chromatin begins to break down coincident with cell death. In cell culture process such as used to produce recombinant proteins, chromatin and its break-down products are expelled into the cell culture media where they may form associations with the constituents of the cell culture media, including the desired recombinant product. The term "chromatin catabolites" may be used to refer to chromatin break-down product. These breakdown products include arrays containing 2-30 or more nucleosomes, individual nucleosomes, nucleosome fragments, DNA, and histone proteins (Gan et al supra, Gagnon et al (2013) supra). "Histone proteins" are understood to represent chromatin catabolites. "DNA" regardless of its size, is understood to represent a species of chromatin catabolites. Individual "nucleosomes" and nucleosome arrays are understood to represent chromatin catabolites.

"Steric exclusion chromatography" refers to a purification method in which retention of an antibody molecule (e.g., an IgG or other antibody product) is mediated by simultaneous mutual steric exclusion of a nonionic organic polymer such as PEG from the hydrophilic surfaces of an antibody and a nonionic particle. It is believed that no direct chemical interaction occurs between the protein surface and the particles surface. This distinctively endows the method with the ability to maintain binding over a wider range of conditions than is possible with traditional chromatography methods such as ion exchange or hydrophobic interaction chromatography.

"Hydrated surface" or "highly hydrated surface" or "hydrophilic surface" refers to surface that interacts strongly with water, potentially through hydrogen bonding, electrostriction, or some combination of the two mechanisms. Such interactions may be mediated by chemical groups such as hydroxyls, negative charges, or positive charges, or uncharged polar groups. The presence of hydratable chemical groups may be a basic feature of the native composition of a given material, such as a particle or convective chromatography material, or it may be added or enhanced by chemical modification to immobilize such groups on the surface, including but not limited to carbohydrates and ureides. So-called hydrophobic surfaces are generally considered not to be highly hydrated, but surfaces that include strongly hydratable groups in combination with hydrophobic residues may nevertheless be sufficiently hydrated to practice the methods disclosed herein.

"Aggregate(s)" refers to an association of two or more molecules that is stable at physiological conditions and may remain stable over a wide range of pH and conductivity conditions. Aggregates frequently comprise at least one biomolecule such as a protein, nucleic acid, or lipid and another molecule or metal ion. The association may occur through any type or any combination of chemical interactions. Aggregates of antibodies can be classified into two categories: "Homo-aggregates" refers to a stable association of two or more antibody molecules; "Hetero-aggregates" refers to a stable association of one or more antibody molecules with one or more non-antibody molecules. The non-antibody component may consist of one more entities from the group consisting of a nucleotide, an endotoxin, a metal ion, a protein, a lipid, or a cell culture media component.

"Antibody" refers to an immunoglobulin of the class IgG, IgM, IgA, IgD, or IgE derived from human or other mammalian cell lines, including natural, or genetically modified forms such as humanized, human, single-chain, chimeric, synthetic, recombinant, hybrid, mutated, grafted, and in vitro generated antibodies. "Antibody" may also include-composite forms including but not limited to fusion proteins containing an immunoglobulin moiety, or immunoconjugates created by synthetic linkage of an IgG to another functional moiety, including another antibody, an enzyme, a fluorophore or other signal generating moiety, biotin, a drug, or other functional moiety.

"Antibody Product" refers to a proteinaceous entity at least part of which comprises an antibody or a portion of an antibody. The simplest example is an antibody. Compound examples include Fc-fusion proteins, which are functional non-antibody proteins covalently bound by recombinant means to the Fc portion of an antibody. Another compound example is an antibody conjugate, or immunoconjugate, which consists of an antibody linked to another moiety, most often by synthetic means, to increase the functionality of the antibody, for example making it fluorescent so that it can be used in immunoassays, or binding it to an enzyme for the same purpose, or two a cytotoxin for killing cancer cells, or to other moieties for other purposes. Other antibody products are bivalent compounds (such as fusions between two antibody fragments) having two domains with binding specificities for two separate targets.

"Endotoxin" refers to a toxic heat-stable lipopolysaccharide substance present in the outer membrane of gram-negative bacteria that is released from the cell upon lysis. Endotoxins can be generally acidic due to their high content of phosphate and carboxyl residues, and can be highly hydrophobic due to the fatty acid content of the lipid-A region. Endotoxins can offer extensive opportunity for hydrogen bonding.

"Non-ionic organic polymer" refers to a naturally occurring or synthetic hydrocarbon composed of linked repeating organic subunits that lack charged groups. It may be linear, dominantly linear with some branching, or dominantly branched. Examples suitable to practice the methods disclosed herein include but are not limited to polyethylene glycol (PEG), polypropylene glycol, and polyvinylpyrrolidone (PVP). PEG has a structural formula $HO-(CH_2-CH_2-O)_n-H$. Examples include, but are not limited to compositions with an average polymer molecular weight ranging from less than 100 to more than 10,000 daltons. The average molecular weight of commercial PEG preparations is typically indicated by a hyphenated suffix. For example, PEG-6000 refers to a preparation with an average molecular weight of about 6,000 daltons. The effective concentration of such agents varies with the identity of the polymer and the characteristics of the antibody product being processed by the methods disclosed herein.

"Organic multivalent ion" refers to an organic molecule, ion or salt of natural or synthetic origin that embodies at least one charge and at least one additional chemical functionality, thus rendering it multivalent. In certain embodiments, an organic multivalent ion the at least one additional chemical functionality is an additional charge such that the organic multivalent ion bears two or more like or differing charges. The organic multivalent ion may bear a net positive, net negative, or net neutral charge. Where the organic multivalent ion is net positive it may be provided together with anions such as chlorides, bromides, sulfates, organic acids, lactates, gluconates, and any other anion not incompatible with the method. In certain embodiments certain of the positive charges of the organic multivalent ion are supplied by amine, imine or other nitrogen moieties. The organic multivalent ion may additionally be of mixed chemical character and include hydrophobic residues, other functional moieties and/or it may possess the ability to participate in other types of chemical interactions including, for example, the ability to participate in hydrogen bonds, hydrophobic interactions, pi-pi bonding, metal coordination, and intercalation. Examples of positively charged organic multivalent ions in certain embodiments include but are not limited to the diamino acids, di-, tri, or larger homo- or hetero-peptides, such as polylysine, polyarginine, polyhistidine, polyornithine; polyethyleneimine; polyallylamine; polydimethrine, polymethylacrylamidopropyltrimethylammonia; polydiallyldimethylammonia; polyvinylbenzyltrimethylammonia; polyvinylguanidine; poly(N-ethyl-4-vinylpyridine; DEAE-dextran; DEAE-cellulose; ethacridine (CAS number 442-16-0; 7-ethoxyacridine-3,9-diamine); tris (2-aminoethyl)amine; guanidine; chlorhexidine; alexidine; citricidal, protamine; spermine; spermidine; salmine; chitosan; and variants and derivatives of the foregoing. For example, variants and derivatives of ethacridine are understood to include 9-aminoacridine (aminacrine), 3,6 acridinediamine (proflavin), acrisorcin, acrizane (phenacridane), acridine orange, quinacrine, acricide, acridone, acridine-9-carboxylic acid, acranil (1-[(6-chloro-2-methoxy-9-acridinyl)amino]-3-(diethylamino)-2-propanol dihydrochloride), phenosafranin, phenoxazine, phenothiazine, acriflavine (3,6-diamino-10-methylacridinium, chloride and 3,6-acridineidiamine), and salts thereof (e.g. chlorides, bromides, sulfates, lactates, gluconates.) Another class of effective electropositive multivalent organic ions includes thiazines, such as methylene blue, its derivatives, analogues, and salts thereof. Where the organic multivalent ion is net electronegative it may be provided together with cations such as sodium or potassium, or any other cation not incompatible with the method. In certain embodiments certain of the negative charges of the organic multivalent ion are supplied by carboxyl, phospho, or sulfo moieties. The organic multivalent ion may additionally be of mixed chemical character and include hydrophobic residues, other functional moieties and/or it may possess the ability to participate in other types of chemical interactions including, for example, the ability to participate in hydrogen bonds, hydrophobic interactions, pi-pi bonding, metal coordination, and intercalation. Examples of negatively charged organic multivalent ions in certain embodiments include but are not limited to the fatty acids such as heptanoic acid, heptenoic acid, octanoic acid, octenoic acid, nonanoic acid, nonenoic acid, decanoic acid, methyl blue, anionic polymers, and salts thereof (e.g. chlorides, bromides, sulfates, lactates, gluconates.)

"Polynucleotide" refers to a biopolymer composed of multiple nucleotide monomers covalently bonded in a chain. DNA (deoxyribonucleic acid) and RNA (ribonucleic acid) are examples of polynucleotides. Polynucleotides can have a high propensity for formation of hydrogen bonds.

"Protein" refers to any of a group of complex organic macromolecules that contain carbon, hydrogen, oxygen, nitrogen, and usually sulfur and are composed principally of one or more chains of amino acids linked by peptide bounds. The protein may be of natural or recombinant origin. Proteins may be modified with non-amino acid moieties such as through glycosylation, pegylation, or conjugation with other chemical moieties. Examples of proteins include but are not limited to antibodies, clotting factors, enzymes, and peptide hormones.

"Protein preparation" refers to any aqueous or mostly aqueous solution containing a protein of interest, such as a cell-containing cell culture harvest, a (substantially) cell-free cell culture supernatant, or a solution containing the protein of interest from a stage of purification.

"Surfactant" includes "surface active agents" such as a class of organic molecules that generally embody a hydrophobic portion and a hydrophilic portion, causing them to be referred to as amphiphilic. At sufficient concentrations in aqueous solutions, surfactants can self-associate into clusters with the hydrophobic portions concentrated at the center to minimize contact with water, and the hydrophilic portions radiating outwards to maximize contract with water. In the presence of biological preparations, especially those containing materials that have a hydrophobic character or possess areas of hydrophobic character, the hydrophobic portion of surfactants tend to associate spontaneously with some portions of the hydrophobic material and increase their solubility through the influence of the hydrophilic portion of the surfactant. They may also be used to modulate hydrophobic interactions that occur between differing hydrophobic materials both dissolved in an aqueous solvent. Examples of surfactants suitable for practicing certain embodiments of the methods disclosed herein include but are not limited to nonionic surfactants such as polysorbate surfactants (e.g., Tween 20, Polyoxyethylene (20) sorbitan monolaurate, and Tween 80, Polyoxyethylene (20) sorbitan monooleate) and Triton (e.g., polyethylene glycol p-(1,1,3, 3-tetramethylbutyl)-phenyl ether), and zwitterionic surfactants such as CHAPS (3-[(3-Cholamidopropyl)dimethylammonio]-1-propanesulfonate), CHAPSO (3-[(3-cholamidopropyl)dimethylammonio]-2-hydroxy-1-propanesulfonate), and octyl glucoside (e.g., (2R,3S,4S,5R,6R)-2-(hydroxymethyl)-6-octoxyoxane-3,4,5-triol).

"Synthetic particles" may range in size from less than 100 nm to more than 100 microns. They may be porous or non-porous. They may polymeric, composed for example of polymethacrylates, polyacrylates, agarose, cellulose, dextran, or other polymers, or they may be inorganic, such as silica. They may be of uniform structure throughout, or they may be compound, consisting of an inner core of one material such as a metal alloy or hydrophobic polymer, and coated with an applied surface that is highly hydrated or permits the attachment of chemical groups to produce a highly hydrated surface. "Synthetic particles" may include particles designed for chromatographic applications, or particles intended for applications entirely distinct from the field of chromatography.

"Impure preparation" refers to any aqueous or mostly aqueous solution containing a protein of interest, such as a cell-containing cell culture harvest, a (substantially) cell-free cell culture supernatant, or a cell extract, or a bodily fluid, or a solution containing the protein of interest from a stage of purification.

"Ureide" refers to a cyclic or acyclic organic molecule of natural or synthetic origin that comprises one or more urea moieties or derivatives thereof. In certain embodiments, the methods disclosed herein provides ureides such as urea, uric acid, hydantoin, allantoin (CAS number 97-59-6; alcloxa, aldioxa, hemocane, ureidohydantoin, 5-ureidohydantoin, glyoxylureide, glyoxylic acid diureide, 2,5-dioxo-4-imidazolidinyl urea), purines, and derivatives thereof. In certain embodiments, the methods disclosed herein provides organic molecules of the formula R—CO—NH—CO—NH$_2$ or R—CO—NH—CO—NH—CO—R' or R' R"NH—CO—NR'"R"" where the relevant "R-groups" may be H or any organic moiety.

"Virus" or "virion" refers to an ultramicroscopic (roughly 20 to 300 nm in diameter), metabolically inert, infectious agent that replicates only within the cells of living hosts, mainly bacteria, plants, and animals: composed of an RNA or DNA core, a protein coat, and, in more complex types, a surrounding envelope.

In certain embodiments, steric exclusion chromatography (SXC) is conducted on fluidized hydrophilic nonionic particles. In certain embodiments, the SXC particles are microparticles that may range from less than 10 microns to more than 200 microns. In certain embodiments the SXC particles are nanoparticles that may range in size from less than 10 nm to 1000 nm. In certain embodiments, the SXC particles may be non-porous. In certain embodiments, the SXC particles maybe microporous. In certain embodiments, the SXC particles may be macroporous. In certain embodiments, the SXC particles may be constituted in such a way as to enable their capture on a magnetic surface or in a magnetic field.

In certain embodiments, SXC is conducted on fluidized hydrophilic nonionic particles. In certain embodiments, the SXC particles are microparticles that may range from less than 10 microns to more than 200 microns. In certain embodiments the SXC particles are nanoparticles that may range in size from less than 10 nm to 1000 nm. In certain embodiments, the SXC particles maybe non-porous. In certain embodiments, the SXC particles may be microporous. In certain embodiments, the SXC particles may be macroporous. In certain embodiments, the SXC particles may be constituted in such a way as to enable their capture on a magnetic surface or in a magnetic field.

In certain embodiments, one or more salts other than NaCl may be used in a washing step. Such salts may include so-called chaotropic salts, sometimes referred to as structure-breaking salts, as exemplified by sodium or potassium isothiocyanate, or so-called kosmotropic salts, sometimes referred to as structure-forming salts, as exemplified by ammonium sulfate, sodium citrate, or potassium phosphate.

In certain embodiments, washing agents other than salts may be used in combination with or instead of salt, such as nonionic chaotropes like urea, or nonionic or zwitterionic surfactants such as CHAPS, CHAPSO, octaglucoside, Tween, or Triton; or nonionic organic solvents such as ethylene glycol or propylene glycol; or sugars such as sucrose or sorbitol, or chelating agents. Due to their ionic nature and their, potential to interfere with anion exchange processes, electropositive chelating agents such as TREN may be preferred over electronegative chelating agents such as EDTA. Other washing agents may also be considered, such as amino acids like arginine, with electro-positive-dominant species preferred for the same reason as with chelating agents.

In certain embodiments, the method is performed as a single unit operation.

In certain embodiments, the PEG used to promote retention of the IgG on the steric exclusion chromatography particles may be of an average size of 8 kDa, or 6, or 4, or 3, or 2, or 1 kDa. In certain embodiments, the substance used to promote retention of the IgG on the steric exclusion, chromatography particles may be a polymer other than PEG, for example polypropylene glycol, polyvinyl pyrrolidone, dextran, or another nonionic organic polymer.

In certain embodiments, the desired antibody product is a fully intact antibody such as an IgG with a molecular mass of about 150 kDa.

In certain embodiments, the sample consists of conditioned cell culture supernatant (CCS). In certain embodiments, the CCS is conditioned by centrifugation, or flocculation, or filtration, or some combination of these techniques. In certain embodiments, the CCS is conditioned by more inclusive means, including the use of chemical additives that particularly reduce chromatin content and/or aggregate content of the preparation. In certain embodiments, the CCS is clarified by a method that removes 95% or more of chromatin, and coincidentally achieves substantial removal of non-histone host protein, endotoxin, and virus, and reduction of aggregate content to 1% or less, while supporting antibody recovery of 90-99%.

In certain embodiments, the claimed methods disclosed herein reduces aggregate content. In certain embodiments, the claimed methods disclosed herein reduce the content of antibody fragments.

It will be recognized by the person experienced in the art that many variations of the above processes can be employed without departing from its essential elements. For example, embodiments may involve uncoupling the process steps so that it is conducted in two, or three, or more unit operations.

In certain embodiments, the claimed methods disclosed herein may be preceded by, or followed by, or both preceded and followed by, other purification methods. In some such embodiments, the disclosed methods may be particularly followed by a fractionation method whereby the desired IgG is retained on a surface, so that residual PEG may be washed away and the antibody subsequently eluted from the surface on which it was retained, now free of PEG. In some such embodiments, the surface on which the antibody is retained may be a chromatography medium from the group consisting of a cation exchange chromatography medium, an apatite medium, a mixed mode medium that combines positive charges and hydrophobicity. In one such embodiment, a mixed mode chromatography medium that combines positive charges and hydrophobicity is represented by the commercial chromatography product marketed under the name Capto adhere (GE Healthcare).

In some embodiments, given that the IgG preparation at the end of the disclosed method will contain a non-IgG-precipitating concentration of a nonionic organic polymer, a follow on purification method may be selected specifically to reduce or eliminate that polymer from the preparation. In one such embodiment, the IgG may be bound to at least one electronegative surface, to which the nonionic organic polymer does not bind, and is thereby eliminated. In one such embodiment, the at least one electronegative surface may be a so-called cation exchanger, such as known and marketed for the purpose of performing chromatographic fractionation of proteins, including IgG preparations. In one such embodiment, the cation exchanger may be in the form of a membrane, a monolith, a column of packed particles, or another physical format. In another embodiment, an at least one electronegative surface may consist of a so-called multimodal chromatography material with a surface composition that permits it to participate in hydrophobic and/or hydrogen binding interactions in addition to electrostatic interactions through its electronegativity. In another embodiment, an electropositive chromatography material with a surface composition that also allows it to participate in hydrophobic interactions and hydrogen bonding may be employed. In one such embodiment, a PEG-containing IgG preparation was applied to a column packed with Capto adhere at 1 M NaCl, pH 7.0. The antibody bound, the PEG did not and was thereby eliminated. The antibody was eluted by reducing the NaCl concentration to 0.3M, whereupon the IgG eluted.

In certain embodiments, SXC particles are added to cell culture supernatant containing a monoclonal IgG antibody. Polyethylene glycol (PEG) is added to the level required for the IgG to be retained by the particles. The liquid containing contaminants that are not bound to the particles is removed, for example by filtration through a membrane, and replaced with clean PEG buffer, hereinafter referred to as a wash buffer. Except for the presence of PEG, the buffer formulation is suitable for binding of residual contaminants to the electropositive particles while antibody remains unbound. The liquid is again removed, for example by filtration through a membrane. The SXC particles are suspended in a buffer lacking or deficient in PEG but otherwise similar to the wash buffer, with the result that the IgG dissociates from the particles in a soluble form. The IgG is collected, for example by filtration through a membrane that retains the SXC particles and electropositive particles, which maybe discarded or recycled.

In certain embodiments, SXC particles are added to an impure preparation containing a monoclonal IgG antibody. PEG is added to the level required for the IgG to be retained by the particles in the presence of 0.8 M NaCl, which is also present in solution. The liquid containing contaminants that are not bound to the particles is removed, for example by filtration through a membrane, and replaced with clean PEG-NaCl buffer. The high-salt wash buffer is removed, for example by filtration through a membrane, and is replaced with clean PEG buffer lacking or deficient in NaCl. The wash buffer is removed. The SXC particles are suspended in a buffer lacking or deficient in PEG, with the result that the IgG dissociates from the particles in a soluble form. The IgG is collected for example by filtration through a membrane that retains the SXC particles, which may be discarded or recycled. In some embodiments, particles for SXC are omitted from the process.

In certain embodiments, SXC particles are added to an impure preparation containing a monoclonal IgG antibody. PEG is added to the level required for the IgG to be retained by the particles. The liquid containing contaminants that are not bound to the particles is removed, for example by filtration through a membrane, and replaced with clean PEG buffer that also contains 0.8 M NaCl. The particles are again collected on the membrane while the high-salt buffer is removed, and replaced with clean PEG buffer lacking or deficient in NaCl. The particles are re-collected on the membrane and the buffer is removed. The SXC particles are suspended in a buffer lacking or deficient in PEG, with the result that the IgG dissociates from the particles in a soluble form. The SXC particles are removed by the membrane, while the purified IgG flows through. In some embodiments, particles for SXC are omitted from the process.

In any of the embodiments involving the use of membranes, it will be apparent to the person of ordinary skill in the art that they can be performed in either a so-called dead-end filtration format, or a tangential flow filtration format, where the former may be more convenient for conducting the disclosed methods at lab scale or to develop the most effective buffer conditions, and where the latter may be more appropriate for industrial scale applications, where it may be partially or fully automated.

Additional objects and advantages of the methods disclosed herein will be set forth in part in the description which follows, and in part will be obvious from the description, or may be learned by practicing the methods disclosed herein. The objects and advantages of the methods disclosed herein will be realized and attained by means of the elements and combinations specified in the claims.

It is to be understood that both the foregoing general description and the following detailed description are exemplary and explanatory only and are not restrictive of the methods disclosed herein as claimed.

EXAMPLES

Example 1

Definition of conditions for IgG binding to steric exclusion chromatography media. An experiment was conducted to determine the salt concentration that supports the most effective reduction of host cell proteins from an anti-HER2 monoclonal antibody produced by mammalian cell culture. The experiment was conducted using nonionic hydrophilic starch particles with an average diameter of about 30 microns. The particles were mixed with different aliquots of cell culture supernatant (CCS). The host protein concentration of the CCS was about 243,011 parts per million (ppm). The sample was treated with allantoin, ethacridine, anion exchange particles and cation exchange particles, which reduced the host protein concentration to 165,213 ppm. PEG-6000 was added to a final concentration of 18%. NaCl was then added to different aliquots to produce a series containing 0.0, 0.2, 0.4, 0.8, and 1.0 M. Host cell protein contaminant levels in the treated samples were 15,558 ppm, 1,994 ppm, 662 ppm, 90 ppm, and 266 ppm. Purification at 0.8 M thus represents an improvement of 99.95%; more than a 3 log reduction.

Example 2

Determination of salt concentration for anion exchange treatment. The antibody of example 1 was evaluated by VEAX. Samples were applied to a VEAX column equilibrated in separate experiments at different pH values ranging from 3 to 9 but lacking salt. Samples were also applied to a VEAX column at pH 8 but including different levels of salt from 0 M to 1 M. The most effective contaminant reduction was achieved at pH 8.0 in the absence of salt. Subsequent experiments refined the target pH at 8.2. Performance was inferior at both pH 8.15 and 8.25. Under these conditions, VEAX achieved up to 99.8% reduction of host proteins, including host proteins, DNA, virus, and endotoxin. These conditions defined the conditions for contaminant extraction by anion exchange in conjunction with SXC, for this antibody.

Example 3

Determination of salt concentration for anion exchange treatment. The antibody of experiments 1 and 2 was applied to anion exchange membranes in stacked flat membrane and hollow fiber formats. Contaminant reduction was essentially the same as under the same conditions for VEAX. These experimental results show that integration of SXC with anion exchange membranes can achieve more than 6 logs of purification (99.9999%).

Example 4

Combination of SXC with electropositive particles. HER2 IgG from cell culture supernatant was bound to starch particles in the presence of 19% PEG-6000 at 1 M NaCl. Electropositive particles in the form of Dowex AG1×8 200-400 mesh were also present in an amount of 4% w/v. The fluid was removed by filtration through a membrane with 0.22 micron pores, then replaced with clean buffer containing 19% PEG-6000, 1 M NaCl, and 50 mM Tris, pH 8.0. The fluid was removed and replaced with clean buffer containing 19% PEG-6000, and 50 mM Tris, pH 8.0. This step was repeated, then the fluid removed by filtration. The fluid was replaced with 50 mM Tris, pH 8.0. Host cell proteins were reduced from 142,000 parts per million (ppm) in the original sample to about 120 ppm.

Example 5

Combination of SXC with electropositive particles. The form of example 4 was repeated except that the electropositive particles were not added until the starch particles were washed with 19% PEG-6000, and 50 mM Tris, pH 8.0. The fluid was removed then replaced with 50 mM Tris, pH 8.0 to dissociate the IgG from the SXC particles. Host cell proteins were reduced from 142,000 parts per million (ppm) in the original sample to about less than 1 ppm.

Example 6

Combination of SXC with electropositive particles. The form of example 5 was repeated except using UNOsphere Q particles in place of Dowex particles. Results with reduction of host cell protein were equivalent, but IgG recovery was higher.

Example 7

Combination of SXC with electropositive particles. The form of example 6 was repeated, with the duration of particle exposure after dissociation of the IgG from the SXC particles varied in increments to determine how much time was required to achieve the best results. Results were essentially the same at 30 and 60 minutes, but inferior at lower exposure times.

Example 8

An IgG-containing cell culture harvest containing 275,357 ppm host cell proteins, 5283 ppm DNA, and 13.96% aggregates was conditioned by addition of 1% allantoin, then 0.025% ethacridine, then mixed for 15 minutes. An equal mixture of MacroPrep High Q, MacroPrep High S, Macroprep tButyl, and Chelex-100 (Bio-Rad Laboratories), equilibrated in advance by washing with 50 mM HEPES, 100 mM NaCl, pH 7.0. Equilibrated mixed particles were added to the impure IgG preparation in an amount of 2% (v:v), then mixed overnight at 4-8 degrees C. Solids were removed by microfiltration. 1.25 mg of starch coated 200 nm magnetic particles were added to 20 mL of the conditioned impure IgG preparation. 20 mL of 36% PEG-6000 in 1.6 M NaCl, 50 mM HEPES, pH 7.0 was added gradually while mixing on a vortex mixer at 500 rpm to produce a final concentration of 18% PEG-6000 and 0.8 M NaCl. Vortex mixing was continued for 30 minutes, then the IgG-loaded particles were collected magnetically. The IgG-loaded particles were washed with fresh 50 mM HEPES, 0.8 M NaCl, pH 7.0, and the wash solution was removed. The wash buffer was removed and the particles were washed again in the same manner. The wash buffer was removed, and the antibody was resolubilized in 50 mM HEPES, 1 M NaCl, pH 7. A 1 mL column packed with an electropositive-hydrophobic chromatography medium (Capto adhere, GE Healthcare) and equilibrated to the same conditions. The solubilized IgG was applied to the column, where the IgG bound and some contaminants were understood to have bound, while residual PEG bind. A 5 column volume wash with equilibration buffer was then applied to more thoroughly eliminate unbound components from the system. The IgG was eluted with a 10 column volume linear gradient ending at 50 mM HEPES, 300 mM NaCl, pH 7.0. Purification performance is indicated by the following Table, where post-con indicates post-conditions, post-NP indicates post nanoparticles, and post-CA indicates post Capto adhere. The left-hand value under recovery indicates recovery for that step, while the right-hand value indicates cumulative recovery for previous steps plus that step. bld indicates below limit of detection. For more details refer to Gagnon et al 2014 supra:

| Step | HCP (ppm) | DNA(ppm) | Aggregates (%) | Recovery % |
| --- | --- | --- | --- | --- |
| Harvest | 275,357 | 5,283 | 13.96 | 100/100 |
| Post-con. | 91,275 | 9 | 4.88 | 98/98 |
| Post-NP | 441 | bld | 3.59 | 87/84 |
| Post-C | 2 | bld | <0.05 | 81/69 |

Example 9

An IgG-containing cell culture harvest containing 176,244 ppm host protein contaminants and 19% aggregates was conditioned by addition of 1% allantoin, 4% electropositive metal affinity particles (TREN 40 high, Bio-Works), mixed for 4 hours at room temperature. A sample removed for analysis showed reduction of host proteins to 90,259 ppm, and aggregates to 1.2%. The pH was reduced to 5.2, 0.5% caprylic acid was added, and the mixture incubated for 2 hours. A sample removed for analysis showed host proteins at 1,758 ppm and aggregates at about 0.4%. Solids were removed through an electropositive depth filter (Sartorius PC1). Host proteins were reduced to 135 ppm and aggregates to less than 0.05%. The antibody was purified by precipitation in 18% PEG-6000 at pH 7.0. The precipitate was then washed with 1.8 M ammonium sulphate to remove PEG, then the antibody was resolubilized in 50 mM Hepes, pH 7.0. Host protein was reduced to 32 ppm. After application to an anion exchange chromatography column (UNOsphere Q, Bio-Rad) operated in void exclusion mode at 50 mM Tris, pH 8.0, host protein was reduced to less than 1 ppm. A parallel experiment differing only in the PEG precipitation being conducted in the presence of 800 mM NaCl reduced host protein to less than 1 ppm. The anion exchange step reduced host protein and aggregates to an undetectable level.

Example 10

An IgG-containing cell culture harvest containing 286,010 ppm host. protein contaminants and 23% aggregates was conditioned by addition of 1% allantoin and 0.025% ethacridine, and incubated stirring at room temperature for 1 hour. A 1:1:1 mixture of particles (Chelex-100, MacroPrep tButyl, Macroprep High Q, Bio-Rad) were mixed, equilibrated to physiological conditions, and settled mixed particles were added to the harvest in a combined amount of 5%, then mixed for 2 hours at room temperature. Host protein was reduced to 43,058 ppm and aggregates to 3.4%. In one series of experiments conducted at pH 8.0, the sample was fractionated by precipitation with PEG-6000, in separate experiments where the concentration was 600 mM, 800 mM, 900 mM, and 1000 mM (1 M). The precipitates were then washed in PEG, 50 mM Tris, pH 8.0, after which the antibody was resolubilized in 50 mM Tris, pH 8.0. Host protein in that series was reduced to 51, 55, 45, and 41 ppm respectively. Anion exchange particles in the form of Dowex AG1X2 (Bio-Rad) were added to each sample in an amount of 5% v/v and mixed for 60 minutes. Host protein across the series was reduced to 16, 17, 15, and 13 ppm. Another series of experiments was run, identical in all details except the initial PEG precipitation was performed at pH 7.0. Host protein after the PEG step was 44 ppm for the 600 mM NaCl track, 43 ppm for the 800 mM track, 29 ppm for the 900 mM track, and 31 ppm for the 1000 mM track. After Dowex treatment, host protein was reduced to 20, 17, 12, and 16 ppm respectively.

Example 11

An IgG-containing cell culture harvest containing 286,010 ppm host protein contaminants and 23% aggregates was conditioned by addition of 1% allantoin and 0.025% ethacridine, and incubated stirring at room temperature for 1 hour. A 1:1:1:1 mixture of particles (Chelex-100, MacroPrep tButyl, MacroPrep High Q from Bio-Rad), and electropositive metal affinity particles (TREN 40 high from Bio-Works) were mixed, equilibrated to physiological conditions, and settled mixed particles were added to the harvest in a combined amount of 5%, then mixed for 2 hours at room temperature. Host protein was reduced to 38,061 ppm and aggregates to 1.4%. In a series of experiments conducted at pH 8.0, the sample was fractionated by precipitation with PEG-6000, in separate experiments where the concentration of NaCl was 600 mM, 800 mM, 900 mM, and 1000 mM (1 M). The precipitates were then washed in PEG, 50 mM Tris, pH 8.0, after which the antibody was resolubilized in 50 mM Tris, pH 8.0. Host protein was reduced to 79, 69, 56, and 57 ppm respectively. Anion exchange particles in the form of Dowex AG1X2 (Bio-Rad) were added to each sample in an amount of 5% v/v and mixed for 60 minutes. Host protein across the series was reduced to 18, 17, 16, and 13 ppm. Another series of experiments was run, identical in all details except the initial PEG precipitation was performed at pH 7.0. Host protein after the PEG step was 94 ppm for the 600 mM NaCl track, 62 ppm for the 800 mM track, 67 ppm for the 900 mM track, and 46 ppm for the 1000 mM track. After Dowex treatment, host protein was reduced to 28, 9, 23, and 17 ppm respectively.

Example 12

An IgM containing cell culture harvest containing 321,483 ppm host protein and 26% aggregates was conditioned by addition of 1% allantoin, 0.025% ethacridine, and NaCl to produce a conductivity of 25 mS/cm. The mixture was incubated for 1 hour, solids were removed by centrifugation, and the liquid was flowed through a column packed with equal proportions of MacroPrep tButyl, Macroprep High Q, Macroprep High S, and Chelex 100, where the volumetric ratio of column to harvest was 5%. Host protein was reduced to 73,663 ppm and aggregates were reduced to 0.8%. The sample was fractionated in parallel but separate experiments, both with 13% PEG-6000 at pH 7, one with 100 mM NaCl, the other with 800 mM NaCl. The precipitates were then washed with 13% PEG, 50 mM Hepes, pH 7.0 to remove the excess salt, then the IgM was resolubilized with 50 mM Hepes, pH 7.0. Host protein at 100 mM NaCl was reduced to 7,411 ppm. Host protein at 800 mM NaCl was reduced to 417 ppm. Aggregate content increased to 1.1%. The samples were applied to an anion exchange monolith (CIM QA, BIA Separations) at pH 7.0 and eluted with a sodium chloride gradient. Host proteins in the sample corresponding to PEG precipitation at 100 mM NaCl were reduced to 1,424 ppm. Host proteins in the sample corresponding to PEG precipitation at 800 mM NaCl were reduced to 63 ppm. Aggregates were less than 0.01% for both preparations.

The present methods disclosed herein may be combined with other purification methods to achieve higher levels of purification. Examples of such other purification methods include, but are not limited to, other methods commonly used for purification of IgG, such as protein A and other forms of affinity chromatography, anion exchange chromatography, cation exchange chromatography, hydrophobic interaction chromatography, immobilized metal affinity chromatography, and additional mixed mode chromatography methods; also methods of precipitation, crystallization, and liquid-liquid extraction. It is within the purview of a person of ordinary skill in the art to develop appropriate conditions for the various methods and integrate them with the methods disclosed herein to achieve the necessary purification of a particular antibody.

All references cited herein are incorporated by reference in their entirety and for all purposes to the same extent as if each individual publication or patent or patent application was specifically and individually indicated to be incorporated by reference in its entirety for all purposes. To the extent publications and patents or patent applications incorporated by reference contradict the disclosure contained in the specification, the specification is intended to supersede and/or take precedence over any such contradictory material.

All numbers expressing quantities of ingredients, chromatography conditions, and so forth used in the specification and claims are to be understood as being modified in all instances by the term "about." Accordingly, unless indicated to the contrary, the numerical parameters set forth in the specification and attached claims are approximations that may vary depending upon the desired performance sought to be obtained by the present methods disclosed herein.

Many modifications and variations of this methods disclosed herein can be made without departing from its spirit and scope, as will be apparent to those skilled in the art. The specific embodiments described herein are offered by way of example only and are not meant to be limiting in any way. It is intended that the specification and examples be considered as exemplary only, with the true scope and spirit of the methods disclosed herein being indicated by the following claims.

What is claimed is:

1. A method of purifying an antibody from a preparation comprising:
   (a) providing the preparation comprising an antibody;
   (b) adding allantoin to the preparation to a supersaturating concentration, wherein after adding the allantoin, the preparation is supersaturated with allantoin;
   (c) removing solids from the preparation;
   (d) contacting the preparation with polyethylene glycol (PEG) in an amount that is sufficient to cause the antibody to precipitate or adsorb on a nonionic surface, wherein the PEG has a nominal molecular weight in a range of 4,000 to 8,000 Daltons; and (e) adjusting a salt concentration of the preparation before or during the contacting step, the adjusting step providing a sufficient salt concentration to produce a conductivity between 50 mS/cm and 150 mS/cm.

2. The method of claim 1, comprising, after the contacting, retaining the antibody on a porous membrane, thereby allowing soluble contaminants to pass through the membrane.

3. The method of claim 1, comprising, after the contacting, separating the antibody from soluble contaminants by sedimenting a precipitate of the antibody by means of centrifugation.

4. The method of claim 1, wherein the nonionic surface comprises one selected from the group consisting of a membrane, a monolith, particles, the particles being optionally magnetic, and combinations thereof.

5. The method of claim 1, wherein the method is carried out in a single integrated apparatus.

6. The method of claim 1, wherein the nominal molecular weight of the PEG is in a range from 5,000 Daltons to 6,000 Daltons.

7. The method of claim 1, wherein the salt is selected from the group consisting of sodium chloride, potassium chloride, sodium acetate, potassium acetate, sodium thiocyanate, potassium thiocyanate, guanidinium hydrochloride, and combinations thereof.

8. The method of claim 7, wherein the salt comprises sodium chloride adjusted to a concentration in a range of 0.5 M to 1.5 M.

9. The method of claim 1, further comprising adjusting a pH of the preparation, before or after the contacting, to a range of 5 to 9.

10. The method of claim 1, wherein the preparation is obtained from a biological source selected from the group consisting of a cell culture medium, an extract from cultured organisms, and a bodily fluid.

\* \* \* \* \*